(12) United States Patent
Lawrenson

(10) Patent No.: US 10,117,616 B2
(45) Date of Patent: Nov. 6, 2018

(54) APNEA SAFETY CONTROL

(71) Applicant: KONINKLIJKE PHILIPS N.V., Eindhoven (NL)

(72) Inventor: Matthew John Lawrenson, Bussigny-pres-de-laussane (CH)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/035,512

(22) PCT Filed: Nov. 12, 2014

(86) PCT No.: PCT/EP2014/074304
§ 371 (c)(1),
(2) Date: May 10, 2016

(87) PCT Pub. No.: WO2015/074918
PCT Pub. Date: May 28, 2015

(65) Prior Publication Data
US 2016/0287158 A1    Oct. 6, 2016

(30) Foreign Application Priority Data
Nov. 22, 2013    (EP) .................................... 13193995

(51) Int. Cl.
*G08G 1/01* (2006.01)
*A61B 5/18* (2006.01)
(Continued)

(52) U.S. Cl.
CPC ................ *A61B 5/18* (2013.01); *A61B 3/113* (2013.01); *A61B 5/02416* (2013.01);
(Continued)

(58) Field of Classification Search
None
See application file for complete search history.

(56) References Cited

U.S. PATENT DOCUMENTS 8,200,510 B1 *  6/2012  Berger et al. ..................... 705/3
8,427,326 B2 *  4/2013  Ben David .................... 340/575
(Continued)

FOREIGN PATENT DOCUMENTS

WO    2012001621 A1    1/2012

OTHER PUBLICATIONS

Series et al, "Nasal Pressure Recording in the Diagnosis of Sleep Apnoea Hyponoea Syndrome", Thorax, vol. 54, No. 6, Jun. 1999, pp. 506-510.
(Continued)

*Primary Examiner* — Brent Swarthout

(57) ABSTRACT

The present invention relates to a safety support system (10), comprising a data interface (20) for receiving sleep quality data carrying information on the sleep quality of a person (12), a sleep quality assessment unit (22) for determining a sleep quality indicator being indicative of the sleep quality of the person (12) based on the received sleep quality data and a safety unit (24) for determining machine operation settings for the person (12) based on the sleep quality indicator, said machine operation settings being indicative of an allowed operation of a machine (14) by the person (12). The present invention further relates to a corresponding method and to a machine (14) comprising a safety support system (10) as described above.

17 Claims, 4 Drawing Sheets

(51) Int. Cl.

| | |
|---|---|
| *A61B 5/0402* | (2006.01) |
| *A61B 5/0476* | (2006.01) |
| *A61B 5/0488* | (2006.01) |
| *A61B 5/0496* | (2006.01) |
| *A61B 5/087* | (2006.01) |
| *A61B 5/00* | (2006.01) |
| *B60K 28/06* | (2006.01) |
| *G08B 21/06* | (2006.01) |
| *A61M 16/00* | (2006.01) |
| *A61B 3/113* | (2006.01) |
| *A61B 5/024* | (2006.01) |
| *A61B 5/145* | (2006.01) |
| *A61B 7/00* | (2006.01) |
| *A61B 5/0295* | (2006.01) |
| *A61B 5/08* | (2006.01) |

(52) U.S. Cl.
CPC .......... *A61B 5/0402* (2013.01); *A61B 5/0476* (2013.01); *A61B 5/0488* (2013.01); *A61B 5/0496* (2013.01); *A61B 5/087* (2013.01); *A61B 5/14542* (2013.01); *A61B 5/4815* (2013.01); *A61B 5/4818* (2013.01); *A61B 5/7264* (2013.01); *A61B 5/7282* (2013.01); *A61B 7/003* (2013.01); *A61M 16/0069* (2014.02); *B60K 28/06* (2013.01); *G08B 21/06* (2013.01); *A61B 5/0295* (2013.01); *A61B 5/0826* (2013.01)

(56) References Cited

U.S. PATENT DOCUMENTS

| | | | | |
|---|---|---|---|---|
| 2002/0016653 | A1* | 2/2002 | Levine | B60K 28/16 701/1 |
| 2004/0243013 | A1* | 12/2004 | Kawachi | A61B 5/18 600/509 |
| 2007/0208269 | A1 | 9/2007 | Mumford et al. | |
| 2009/0005652 | A1 | 1/2009 | Kurtz | |
| 2011/0195699 | A1* | 8/2011 | Tadayon | H04B 5/0062 455/418 |
| 2012/0235819 | A1* | 9/2012 | Watkins | A61B 5/18 340/573.1 |
| 2013/0158423 | A1 | 6/2013 | Kapoor | |
| 2013/0204495 | A1* | 8/2013 | Reed | B60W 30/146 701/45 |
| 2017/0337813 | A1* | 11/2017 | Taylor | G08G 1/0141 |

OTHER PUBLICATIONS

Han et al, "Detection of Apneic Events From Single Channel Nasal Airflow Using 2nd Derivative Method", Computer Methods and Programs in Biomedicine, vol. 91, Issue 3, Sep. 2008, pp. 199-207.

El-Solh et al, "Validity of Neural Network in Sleep Apnea", Sleep, vol. 22, No. 1, Feb. 1999, pp. 105-111.

Beddit Sleep Tracker; The Invisible Sleep Tracker, Downloaded from http://www.beddit.com on May 10, 2016, pp. 1-10.

Up by Jawbone, A Smarter Fitness Tracker for a Fitter You, Downloaded From https://jawbone.com/up on May 10, 2016, pp. 1-13.

Sleep Cycle Alarm Clock, Downloaded From http://www.sleepcycle.com on May 10, 2016, pp. 1-4.

Chen et al, "Daytime Sleepiness and Its Determining Factors in Chinese Obstructive Sleep Apnea Patients", Sleep Breath, vol. 15, 2011, pp. 129-135.

Hida et al, "Home Sleep Monitor for Detecting Apnea Episodes by Nasal Flow and Trachael Sound Recording", Tohoku J. Exp. Med, vol. 156, Suppl., 1988, pp. 137-142.

Waxman et al, "Automated Prediction of Apnea and Hypopnea, Using a Lamstar Artificial Neural Network", American Journal of Respiratory Critical Care Medicine, vol. 181, Issue 7, 2010, pp. 727-733.

Kerr et al, "Driving With Diabetes in the Future: In-Vehicle Medical Monitoring", Journal of Diabetes Science and Technology, vol. 4, Issue 2, Mar. 2010, pp. 464-469.

"Driver Fitness Medical Guidelines", Sep. 2009, pp. 10159.

"No Judgement Thread: Do You DJ High or Drunk", DJing Discussion, 2012, pp. 1-6.

* cited by examiner

APNEA SAFETY CONTROL

CROSS-REFERENCE TO PRIOR APPLICATIONS

This application is the U.S. National Phase application under 35 U.S.C. § 371 of International Application Serial No. PCT/EP2014/074304, filed on Nov. 12, 2014, which claims the benefit European Application Serial No. 13193995.1, filed on Nov. 22, 2013. These applications are hereby incorporated by reference herein.

FIELD OF THE INVENTION

The present invention relates to a safety support system and a corresponding method as well as to a machine being controlled based on a safety support system.

BACKGROUND OF THE INVENTION

Obstructive Sleep Apnea (OSA) refers to a sleep disorder usually caused by an obstruction or partial obstruction of the upper airway and a restriction of the air passage into the lungs. It is characterized by repetitive pauses in breathing or instances of shallow and infrequent breathing during sleep and it is usually associated with a reduction in blood oxygen saturation. Such pauses in breathing, called apneas, typically last 20 to 40 seconds. Less severe but also often causing a decreased amount of air movement into the lungs and a drop in oxygen level in the blood are episodes of overly shallow breathing or an abnormally low respiratory rate, called hypopnea. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied by snoring.

Different invasive and non-invasive treatments for OSA are known. One of the most powerful non-invasive treatments is the usage of continuous positive airway pressure (CPAP) or bilevel positive airway pressure (BiPAP) in which the patient uses a machine (CPAP machine or BiPAP machine) that blows cleaned air, oxygen or any modification thereof in a pressurized or unpressurized way through the airway of the patient in order to keep it open.

One effect of OSA and also of the treatment with positive airway pressure (PAP) machines is that the patient's quality of sleep can be negatively affected and the patient may feel less rested in the morning. OSA patients may therefore run at risk to make mistakes due to drowsiness during the day. Such mistakes may especially be dangerous if a drowsy person operates a machine, e.g. a car.

A possible approach to cope with this is the concept of in-vehicle medical monitoring. In Kerr et al., "Driving with Diabetes in the Future: In-Vehicle Medical Monitoring", Journal of Diabetes Science and Technology, Volume 4, Issue 2, March 2010, a study on diabetes patients is presented. The authors argue that driving a vehicle requires complex coordination of cognitive, motor, and sensory skills. These aspects can be affected adversely by diabetes per se, with hypoglycemia being the main concern for people with diabetes who drive. The authors present a concept of using the motor vehicle as a device to collect and deliver physiological and clinical information, which, in turn, may enable more people to drive more safely by reducing the chances of medical mishaps behind the wheel. This is particularly relevant for people living with diabetes who are at risk from a number of medical conditions that have the potential to have an impact on safe driving. The development of in-vehicle medical monitoring presents a new opportunity for novel collaborations between two industries, which have safety as a core value.

Further, in US 2013/0158423 A1, a mobile wellness device is disclosed. There is presented a system for acquiring electrical footprint of the heart, electrocardiogram (ECG) and heart rate variability monitoring, incorporated into a mobile device accessory. The ECG signal is conveniently acquired and transmitted to a server via the mobile device, offering accurate heart rate variability biofeedback measurement which is portable and comfortable during normal daily life. The presented system is claimed to provide a reliable tool for applications such as wellness, meditation, relaxation, sports and fitness training, and stress-relief therapy where accurate heart rate variability measurement is desired.

However, in spite the efforts on in-vehicle monitoring or mobile monitoring devices, the problem remains that it may be dangerous for OSA patients and bystanders if the OSA patient suffers from drowsiness during driving a car or operating another machine.

US 2009/0005652 A1 discloses methods and systems for controlling a subject's access to an activity based on a sleep quality index. The sleep quality index may include various physiological data relating to the subject, including current and historical physiological data, previous sleep quality indices for the subject. The subject's access to the activity may also be restricted based on personal characteristics of the subjects or on the identity of the subject.

SUMMARY OF THE INVENTION

It is an object of the present invention to provide an improved safety support system and a corresponding method that overcome the above-mentioned deficiencies.

In a first aspect of the present invention a safety support system is presented. The system comprises:
  a data interface for receiving sleep quality data carrying information on the sleep quality of a person,
  a sleep quality assessment unit for determining a sleep quality indicator being indicative of the sleep quality of the person based on the received sleep quality data; and
  a safety unit for determining machine operation settings for the person based on the sleep quality indicator, said machine operation settings being indicative of an allowed operation of a machine by the person, wherein said machine operation settings include a value which describes an accessible functional range defining which function of the machine can be accessed by the person and to which extent it can be accessed.

In another aspect, a safety support method is presented that comprises the steps of:
  receiving sleep quality data carrying information on the sleep quality of a person,
  determining a sleep quality indicator being indicative of the sleep quality of the person based on the received sleep quality data; and
  determining machine operation settings for the person based on the sleep quality indicator, said machine operation settings being indicative of an allowed operation of a machine by the person, wherein said machine operation settings include a value which describes an accessible functional range defining which function of the machine can be accessed by the person and to which extent it can be accessed.

In yet another aspect, a machine is presented that comprises
a safety system interface for communicating with a safety support system as described above and for receiving machine operation settings being indicative of an allowed operation of the machine by a person, wherein said machine operation settings include a value which describes an accessible functional range defining which function of the machine can be accessed by the person and to which extent it can be accessed; and
an interlock device for restricting the operation of the machine to the allowed operation based on said value included in the machine operation settings.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method has similar and/or identical preferred embodiments as the claimed system and as defined in the dependent claims.

A safety support system for increasing safety of machine users and bystanders is presented herein. Sleep quality data of a person are received and it is determined whether this person has slept well enough to allow him or her to operate a machine such as a vehicle or not. This decision is based on a sleep quality indicator that indicates how well a person has slept. If the system determines that the person's sleep quality was not sufficient, the operation of the machine can be restricted. In particular, there are determined machine operation settings that indicate how or if at all the person may operate the machine. Possible restrictions may include a maximum usage duration, velocity, load or number of passengers to take along etc.

One advantage of the present invention is that the relevant data, i.e. the data carrying information on the sleep quality of a person, form the basis for the decision of whether or not it is safe for the person to operate a machine. The determination of the machine operation settings is based on input that is directly related to the sleep quality, which, according to the system presented herein, is used as an indicator for the current drowsiness of a person.

Another advantage of the present invention is that a plurality of different data can be used in order to assess the sleep quality of the person. The determined machine operation settings, i.e. the information how a person may use the machine, can then either be used to directly restrict or limit the use of a machine or can be further processed, e.g., for providing feedback to the person that he or she should reconsider whether or not to use a machine. Thus, it may be possible to directly get to a decision and restrict a machine accordingly or to merely suggest to a person to operate a machine as indicated by the determined machine operation settings.

A machine including a safety support system as presented herein may allow increasing the safety of both the person using the machine as well as other persons in the vicinity of the machine. It may, e.g., be possible that an insurance company requires an insurant to use a system as claimed herein in order to obtain a reduction of the insurance rate.

In a preferred embodiment, the system further comprises a machine interface for communicating with the machine and for controlling the operation of the machine based on the determined machine operation settings.

If the determined machine operation settings are provided to a machine via such an interface, the machine can directly implement the determined machine operation settings, i.e. restrict its functionality based thereupon. This may, e.g., be used in applications where not only the safety of the person operating the machine is endangered if the person operating the machine is tired, but also the safety of bystanders. Application scenarios may include machines that potentially endanger a high number of persons such as airplanes, trains or the like. Then, it may be particularly useful to directly communicate the determined machine operation settings to a machine via a suitable interface. An advantage of this embodiment is that no input or compliance of the person using the safety support system is required. The system can directly provide the determined machine operation settings to a machine through the machine interface.

In another embodiment, the sleep quality data include data determined during a time period prior to an intended operation of the machine by a person.

In contrast to other monitoring systems, the present invention makes use of sleep quality data carrying information on the sleep quality of a person. Such data are advantageously determined during a time period prior to an intended operation of a machine, such as the night before or some hours before the person intends to operate the machine. If a system makes use of real-time data, i.e. data determined online while a person operates a machine, it may already be too late to prevent dangerous situations as the person is already operating the machine. According to this embodiment, the sleep quality data are determined before the person operates the machine, i.e. prior to an intended operation. This allows coming to a decision whether at all or to what extent a person may operate a machine prior to the person beginning to operate the machine. Thereby, it may be possible to prevent accidents due to tired persons operating machines.

In a further embodiment, the sleep quality data include a polysomnogram of the person that includes one or more signals representative of an electroencephalogram, an electrooculogram, an electromyogram, an electrocardiogram, an oral and/or nasal airflow, snoring loudness, a level of eye movement and a level of body movement.

Such a polysomnogram is usually the result of a sleep study carried out in a sleep laboratory. A polysomnogram may, however, also be determined at home. Depending on the available sensors, the polysomnogram may comprise different signals. As used herein, a signal corresponds to the development of a measure over time. The plurality of signals forms the sleep quality data. Each of the signals can carry information on the sleep quality of the person. The significance of each signal could be determined from an experimental study or based on the assessment of a medical practitioner (i.e. a physician, nurse, caretaker etc.). An electroencephalogram, electrooculogram, electromyogram or electrocardiogram is usually measured by means of one or more electrodes attached to different body parts of a person. The oral and/or nasal airflow can, e.g., be measured by means of a flow sensor arranged in proximity of the person's airway. The snoring loudness can, e.g., be determined by means of an acoustic sensor, i.e. a microphone. The level or eye movement can, e.g., be determined by means of a camera directed at the eyes or pupils of the person. A level of body movement can, e.g., be determined by means of an acceleration sensor attached to the person or to an object being in contact with the person. All these different signals may carry information on how good or bad a person sleeps.

According to another embodiment, the sleep quality data include data carrying direct or indirect information on apnea and hypopnea events during a sleep period of a person and the sleep quality assessment unit is configured to determine an estimate or an apnea-hypopnea-index of the person.

Herein direct information on apnea or hypopnea events refer to data directly representing the number, intensity or the duration of apnea or hypopnea events as, e.g., determined by a dedicated system (e.g. a system included in a PAP machine). In contrast thereto, indirect information rather refers to information from which an estimate of such parameters can be obtained such as a nasal airflow or a sound signal that requires further processing in order to determine the parameter itself. If such information is available, one possibility of assessing the sleep quality of a person is to determine the apnea-hypopnea-index (AHI) of the person. This index is usually calculated by dividing the number of events (apneas and hypopneas) by the time of sleep. This AHI value can be used as a measure for the sleep quality of the person. One possible definition for apnea events to be included in the AHI is events that last at least ten seconds and that are associated with a predefined decrease in blood oxygenation. One possible definition for a hypopnea event is a respiratory rate under the predefined threshold. The main advantage of this embodiment is that the AHI is often used as standard measure in sleep therapy and represents a more or less widely accepted sleep quality indicator. Also, different PAP devices have a built-in AHI-functionality.

The AHI is often determined by recording and evaluating the nasal pressure or airflow. The standard clinical test to determine the AHI makes use of a polysomnogram as discussed above, allowing to accurately identifying apnea and hypopnea events of a person. A study on determining the AHI based on the nasal pressure is presented in Series F. et al, Nasal pressure recording in the diagnosis of sleep apnoea hypopnoea syndrome, Thorax. 1999 June; 54(6):506-10. A study on the use of the nasal airflow is presented in Han et al., Detection of apneic events from single channel nasal airflow using 2nd derivative method, Computer Methods and Programs in Biomedicine Volume 91, Issue 3, Pages 199-207, September 2008.

According to a preferred embodiment, the sleep quality assessment unit is configured to determine the sleep quality indicator based on a neural network analysis.

Such a neural network or artificial neural network corresponds to a learning algorithm that is trained based on available data and associated output to deliver a predicted output for new data with initially unknown output. Usually, an appropriate network design has to be chosen wherein a number and a connection structure of so-called neurons or interconnected neurons are defined. Then a training phase in which available sleep quality data are associated with a sleep quality indicator as determined by a medical practitioner is carried out, i.e. available sleep quality data and their associated output (sleep quality indicator) are used to train the network. This network can then be used for predicting the outcome (sleep quality indicator) of other input data (sleep quality data). In particular, a neural network can be used to determine or predict the AHI of a patient. For instance, an approach to use of neural networks for predicting the AHI is presented in el-Solh A A et al., Validity of neural network in sleep apnea, Sleep. 1999 Feb. 1; 22(1):105-11.

In a preferred embodiment, the safety unit is configured to compare the determined sleep quality indicator with a threshold value.

This threshold value may thereby particularly correspond to a predetermined threshold value, e.g. determined by a medical practitioner in a study or during an evaluation of the person. Alternatively, the threshold value may be continuously updated (moving average or the like).

According to this embodiment, the determination of the machine operation settings is based on a comparison of the determined sleep quality indicator to a threshold value. This has the advantage that a simple and comprehensible approach for determining the machine operation settings can be defined. If the person has slept well enough, i.e. the sleep quality indicator is above the threshold value, one set of machine operation settings is determined, if the person has not slept well enough, i.e. the sleep quality indicator is below the threshold value, another set of machine operation settings is returned. For determining an appropriate threshold value a survey-based assessment of sleepiness may be used. For instance, the Epworth Sleepiness Score and Oxford Sleep Resistance test could be used to set a threshold. Alternatively, a medical practitioner (or the person himself) could set an appropriate threshold value. Still further, the person's drowsiness during the day could be monitored using physiological monitors and correlate that to their previous night's sleep.

According to a non-claimed embodiment, the machine operation settings may include a binary decision parameter indicating that the person is allowed to operate the machine if the determined sleep quality indicator is above a threshold value. According to this embodiment, the machine operation settings particularly indicate whether or not the person should or may operate the machine. Thus, a binary decision is returned. One advantage of determining a binary decision parameter is that further processing is facilitated. For instance, a warning may be issued to the person that he should not operate the machine or the machine operation could be completely prohibited.

According to yet another embodiment, the data interface is configured to further receive medical history data of the person in addition to the sleep quality data, said medical history data being indicative of a progress of a medical condition of the person and the sleep quality assessment unit is configured to determine the sleep quality indicator based on the received sleep quality data and the medical history data.

These medical history data are used in addition to the sleep quality data. One particular advantage of additionally including medical history data is that person-specific circumstances and conditions could be considered when determining the sleep quality indicator. For instance, one person may still sleep well enough to operate a machine in spite of a high AHI while another person with a comparable AHI may already feel very drowsy. This may be because the one person has been used to suffering from apneas for a long time or because this person's physiological condition allows him to sleep well in spite of frequent interruptions. Such information may be determined, e.g., by a medical practitioner who knows the person and who can judge how well or bad a person has slept. On the other hand, a person suffering from OSA due to a temporary medical condition may not be used to the bad sleep and may thereby not be in a condition to operate a machine in spite of a comparably low AHI. Such effects can be compensated by including medical history data of the person. These medical history data could, e.g., be provided by a medical practitioner or could be determined based on an evaluation of the condition of the person in standardized tests or the like.

In yet another embodiment, the safety support system further comprises at least one of the following sensors connected to the data interface for capturing at least one sensor signal, which at least one sensor signal at least partly forms the sleep quality data: an acceleration sensor for capturing a sensor signal indicative of a movement of the person, a camera sensor for capturing a sensor signal indicative of a movement of the eyes of the person, a flow sensor for capturing a sensor signal indicative of the breathing of the person, an acoustic sensor for capturing a sensor signal indicative of breathing sounds of the person, a blood oxygenation sensor for capturing a sensor signal indicative of the blood oxygen saturation of the person and a photoplethysmography sensor for capturing a sensor signal indicative of a vital sign of the person.

According to this embodiment at least one sensor is comprised in the safety support system. One advantage thereof is that an integrated device could be realized allowing implementing the functionality of the safety support system in the form of a system in the box, e.g. in form of a portable device. It may be possible to only use the sensor signal of the at least one comprised sensor and thereby not require further external data input.

In yet another preferred embodiment, the system further comprises a pressure support system including a pressure generator for generating a pressurized flow of breathable gas, a patient interface for delivering the pressurized flow of breathable gas to the person and a flow sensor for capturing a sensor signal indicative of the breathing of the person, wherein the flow sensor is connected to the data interface and the sensor signal at least partly forms the sleep quality data.

One advantage of integrating the safety support system with a pressure support system such as a PAP machine is that the required sleep quality data can be directly obtained from a flow sensor that measures a signal representative of the breathing of the person. As the person is already connected to a patient interface, no further sensor equipment is required. According to this embodiment, the safety support system can be seen as an improved PAP machine providing additional functionality.

In yet another embodiment, the safety support system as described above further comprises an interlock device for restricting the operation of a machine to the allowed operation based on the determined machine operation settings.

Thereby, the safety support system is directly connected to the necessary equipment for restricting the operation of a machine. An interlock device thereby refers to an electronic or mechanical mechanism that interacts with the machine and that is capable of restricting, i.e. limiting, or preventing the operation of a machine, e.g. an ignition interlock that prevents the ignition of the motor of a vehicle. The advantage is that the communication with the machine may be facilitated and carried out efficiently.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
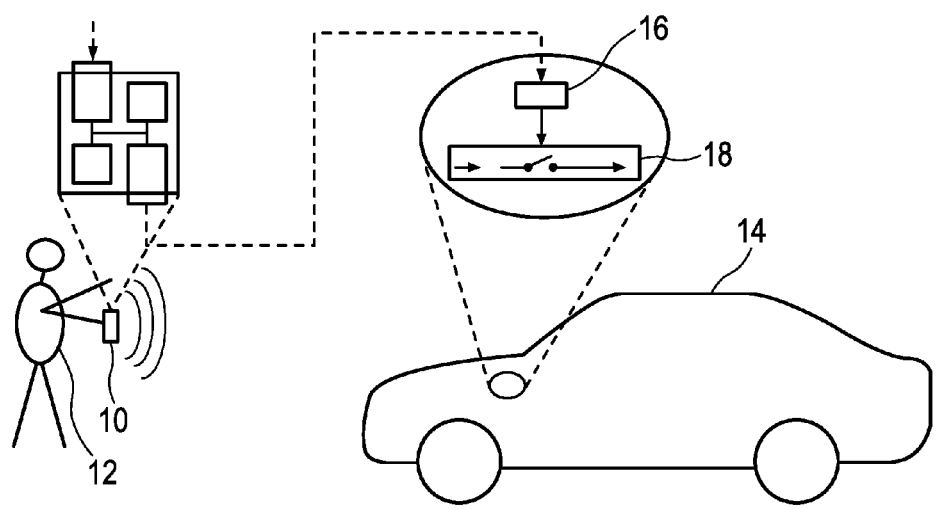
FIG. 1 shows an overview of an exemplary application scenario in which a safety support according to the present invention is used to restrict the use of a car.

Sleep disorders such as obstructive sleep apnea (OSA) have the effect that affected persons or patients often sleep bad, may suffer from drowsiness during the day and have higher levels of daytime sleepiness than non-affected persons. Driving a car or operating another machine in such a condition, e.g. after a bad night, can result in dangerous situations and a higher risk of accidents for both the person himself and bystanders in the vicinity of the car or the machine. It is the goal of the present invention to increase the safety of a person intending to operate a machine and other persons by providing a safety support system.

As used herein, sleep quality data may refer to data carrying information on the sleep of a person. Sleep quality data particularly refer to different kinds of sensor data captured for a sleeping person during the night or during a sleep period. Sleep quality data can also be provided by a physician or medical support personal.

A sleep quality indicator as used herein particularly refers to a parameter describing how well or bad a person has slept. A person that sleeps well, i.e. has a high sleep quality, will usually feel more awake or relaxed the other day compared to a person sleeping bad (low sleep quality). The sleep quality indicator describes the sleep quality, i.e. gives a measure for it, and may be indicated on an absolute or relative scale (relative to previous values for the person or to the sleep quality of other persons). For instance, a percentage value may be used. Alternatively a value on an absolute scale, e.g. 1-5 or good/bad may be used. Further alternatively or additionally, an absolute value such as the number of hours the person has slept, how often the person woke up during the night or the like may be used.

Machine operation settings as used herein particularly refer to usage criteria defining how or to what extent a machine can be operated. Particularly, machine operation settings refer to restrictions or constraints on the operation of the machine. Machine operation settings may, e.g., indicate that a person is not allowed to use all functionality of the machine. Machine operation settings may include values describing the accessible functional range, i.e. which function of a machine can be accessed to which extent (e.g. time, force, velocity, duration, frequency, etc.). Alternatively, the machine operation settings could include a binary value indicating whether or not at all the machine may be operated.

Medical history data as used herein refer to any kind of data indicative of the medical history of a patient, e.g. any piece of information taken from the patient's clinical records. Medical history data may thereby refer to both quantifiable as well as to non-quantifiable data. Medical history data may also be determined based on expert input from a medical practitioner. In contrast to sleep quality data, medical history data particularly refers to all data that cannot be determined online, e.g. by a sensor, but that need to be interpreted. Also medical history data may refer to sensor data that have been determined at an earlier time.

FIG. 1 illustrates an application of a safety support system 10 according to the present invention. A person's 12 sleep quality is assessed and a sleep quality indicator indicative of the sleep quality of the person 12 is determined. Based on this sleep quality indicator machine operation settings are determined that are indicative of how the person 12 may operate machine 14, i.e. the car according to the example illustrated in FIG. 1. For this the safety support system 10 may communicate with the machine 14 in particular through an appropriate safety system interface 16 in the machine 14 being connected to an interlock device 18 for restricting the operation of the machine 14 to the allowed operation. In the present example, the interlock device 18 may particularly be represented by an ignition interlock that electronically or mechanically prevents an ignition of the engine of the car 14.

Apart from restricting the driving of a vehicle such as a car, a safety support system 10 as presented herein may particularly be of use when trying to increase the safety in industrial facilities where robots are operated, on construction sites where cranes are used, for aircraft, for trains as well as or for other machines that potentially put their operator and/or involved other persons in danger. The determined machine operation setting may particularly include a binary parameter indicating whether or not the person may at all operate the machine or not. The machine operation settings may, however, also include parameters such as the maximum operation duration, number of passengers to take along, payload, operation duration without rest, driving velocity, operation speed, required pauses or surveillance/help etc.

Figure 2:
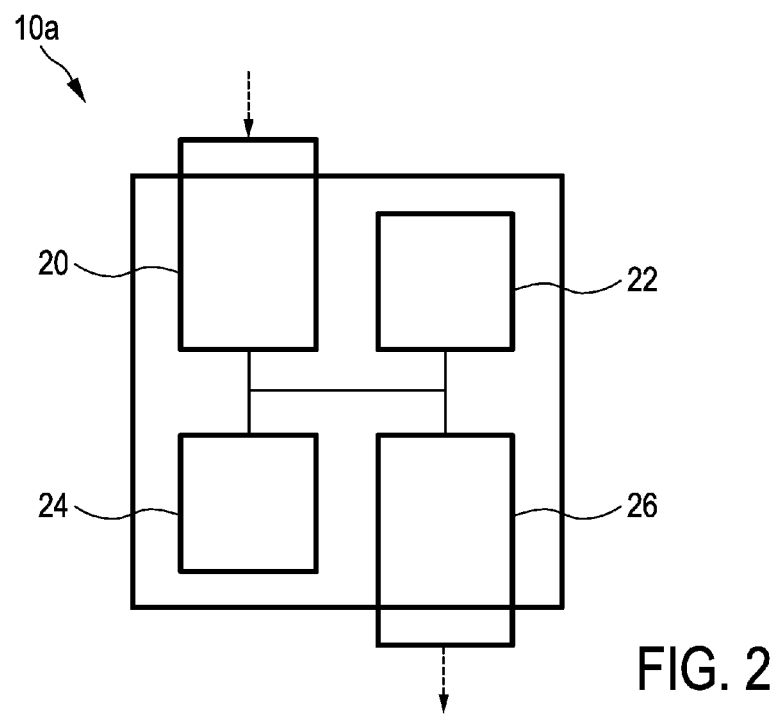
FIG. 2 schematically illustrates an embodiment of a safety support system according to the present invention.

FIG. 2 schematically illustrates a first embodiment 10a of a safety support system 10 according to the present invention. This safety support system 10a comprises a data interface 20 for receiving sleep quality data carrying information on the sleep quality of a person. Such a data interface 20 may be represented by any kind of standard or non-standard serial or parallel, wired or wireless interface that allows receiving data. Depending on the context in which the safety support system 10a is used, the data interface 20 may particularly be connected to any kind of sensor equipment, a database, a medical information system or also a human machine interface. Thereby, the connection may be direct or via an intermediate system, such as the Internet or another network.

The system 10a further comprises a sleep quality assessment unit 22 for determining a sleep quality indicator being indicative of the sleep quality of the person 10 based on the received sleep quality data. Depending on the received sleep quality data, various alternatives for determining a sleep quality indicator exist. A sleep quality indicator may, e.g., correspond to a value on an absolute or relative scale, a multidimensional value assessing the sleep quality in different dimensions (e.g. sleep duration, wake-up events, interruptions, number/intensity/duration of apnea/hypopnea events, heart rate variability, used medication, etc.).

Still further, the system 10a comprises a safety unit 24 for determining machine operation settings for the person based on the sleep quality indicator. Therein, the machine operation settings are indicative of an allowed operation of a machine by the person. The machine operation settings may correspond to a binary indication of whether or not the person is allowed to operate the machine at all, a time indication indicating when or how long a person may operate the machine, a maximum velocity of a vehicle, a maximum load of a crane, a maximum size of a machine, a minimum required resting time of the person, a maximum speed of any moving part of the machine, etc. These determined machine operation settings then form the basis for controlling the operation of a machine.

For this, the system 10a further comprises a machine interface 26 for communicating with a machine. Comparable to the data interface 20, said machine interface 26 may also be represented by any kind of serial or parallel, wired or wireless, standard or non-standard data communication interface. The communication with the machine may work directly or via an intermediate system, such as the Internet or another network. It may also be possible that the communication is carried out via a mobile device or personal information device such as a smartphone, which could additionally allow carrying a code without having a network connection (i.e. in offline operation mode).

The interfaces 20, 26 and the units 22, 24 may thereby be implemented separately, e.g. as application specific integrated circuits (ASIC) or field programmable gate arrays (FPGA) or standard microcontroller units (MCU). The different interfaces 20, 26 and units 22, 24 may be implemented separately or in different combinations in the form of one or more processors or the like. The interfaces 20, 26 and units 22, 24 may be partly or completely implemented in hard- or software. Alternatively, some or all of the interfaces 20, 26 and units 22, 24 may be part of an Internet-based (server-based) system or may be implemented in a personal computer.

In a preferred embodiment of the present invention, the sleep quality assessment unit 22 is configured to determine an apnea-hypopnea-index (AHI) based on the received sleep quality data. Such an AHI or an estimate therefore is a standard measure for the sleep quality of a patient suffering from OSA and indicates the number of apnea and/or hypopnea events during a predefined time span. An AHI of 15 may, for instance, correspond to a total number of 15 apnea or hypopnea events per hour. In order to determine the AHI, one standard method is the use of overnight polysomnography (OPG). This typically involves a suite of tests and is currently often considered to not really be ready for home usage. However, the used sensor equipment is available for home use and it may very well be possible to apply polysomnography to a patient at home.

Also, it is possible to make use of a neural network analysis in order to determine the AHI based on different sleep quality data and an appropriately trained neural network (artificial neural network). Also, other machine learning based approaches may be used for determining the AHI or another sleep quality indicator.

The safety support system 10a may, e.g., be implemented in the form of a handheld device (smartphone, wrist band, watch, etc.) that interacts with a machine, in the form of an Internet-based system that interacts with a machine and/or a medical practitioner, in the form of an alarm clock that wakes up a patient earlier if it comes to the conclusion that the person should rather not drive a car but use public transport to get to work or in various other forms. It may also be possible that activities/resources of the person are re-organized depending on the determined machine operating settings. If, e.g., the system is used to prevent tired people from using a machine in a factory then the determined information could directly be used to make sure a replacement person is organized to operate the machine. Such functionality may be provided by an additional system or may be integrated in a further embodiment of the present invention.

Figure 3:
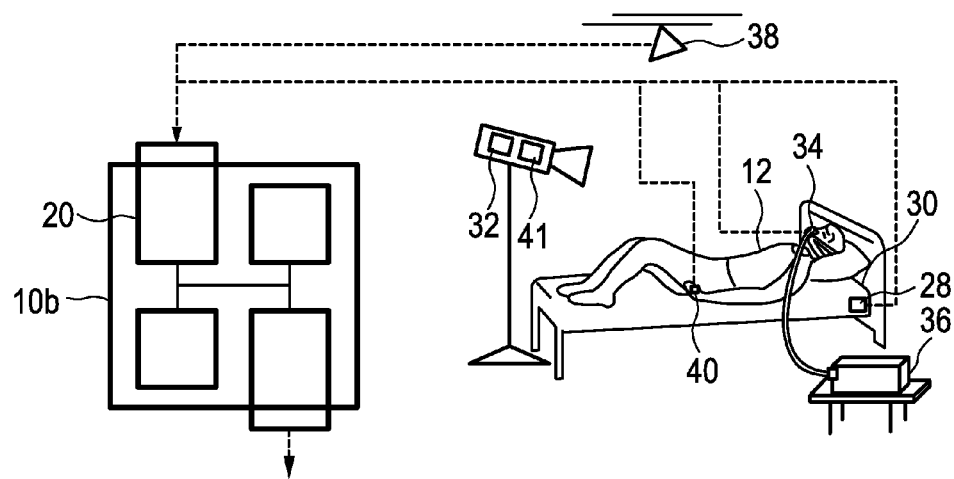
FIG. 3 schematically illustrates a further embodiment of the safety support system according to the present invention.
Figure 4:
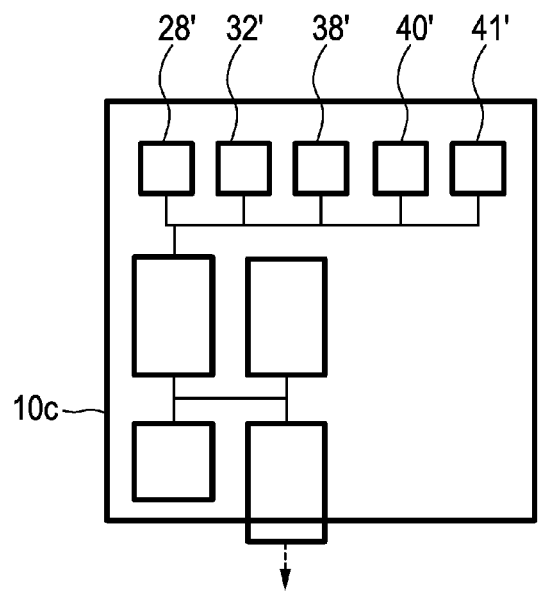
FIG. 4 schematically illustrates yet another embodiment of the system according to the present invention.

FIG. 3 illustrates another preferred embodiment 10b of a safety system 10 according to the present invention. Therein, the data interface 20 is connected to a plurality of sensors capturing sensor signals which at least partly form the sleep quality data.

There is illustrated an acceleration sensor 28 being attached to a person's 12 bed 30 (or chair). Such an acceleration sensor 28 can measure the movement of the person 12 and deduce therefrom whether the person 12 is asleep or not. For this, the acceleration sensor 28 may be attached directly to the person 12 or indirectly to clothing or furniture that is in contact with the person 12. Such an acceleration sensor 28 may output a one- or multidimensional sensor signal, particularly a sensor signal being representative of movements of the person 12 or his/her movement intensity. High movement intensity may be indicative of a bad sleep.

Further, there is illustrated in FIG. 3 a camera sensor 32 for capturing a sensor signal indicative of a movement of the eyes of the person 12. Such a camera signal may correspond to an analog or digital signal from a CMOS or CCD sensor possibly preprocessed in an image processing device for extracting specific information from the captured image signal. For instance, an image sequence or video signal may be processed in order to determine a photoplethysmography signal representing a vital sign of the person (heart rate, blood oxygenation, breathing rate, etc.). It may also be possible to use image processing methods to extract information on the eye movements of the person 12. Usually, a person showing a high level of eye movements does not sleep well.

Further, there is illustrated a flow sensor 34 for capturing a sensor signal indicative of the breathing of the person 12. In the illustrated example, the flow sensor 34 is integrated in a patient interface of a breathing support system 36 such as a PAP machine (e.g. CPAP or BiPAP machine). Such a flow sensor 34 may particularly capture a signal indicative of how much the person 12 breathes, how often the person 12 breathes, the number of apnea/hypopnea events, the required breathing support, the pressure of the provided breathing support, etc.

Still further, there is illustrated an acoustic sensor 38 for capturing a sensor signal indicative of breathing sounds of the person 12. Breathing sounds particularly refer to the snoring sounds. Breathing sounds, however, can also be indicative of the airflow (oral or nasal airflow), i.e. the sound of air going in and out of can give an indication of how much air is going in and out. Such an acoustic sensor 38 may particularly be represented by a microphone being mounted in the vicinity of the person 12 or the person's 12 head in order to capture all noise and extract therefrom information on the snoring (loudness, intensity, frequency, etc.) or on the airflow. This acoustic sensor 38 may also include a preprocessing device for preprocessing the captured signal.

Still further, FIG. 3 shows a blood oxygenation sensor 40 for capturing a sensor signal indicative of the blood oxygen saturation of the person 12. As an example, there is illustrated a finger clip pulse oximeter 40. However, other sensors providing equivalent or comparable information may be used.

Still further, a photoplethysmography (PPG) sensor 41 is illustrated. Such a PPG sensor 41 allows deriving a PPG waveform from fluctuations in brightness or intensity values captured by means of a photosensor. From this PPG waveform information on a vital sign of the patient 12, in particular the heart rate, the blood oxygen saturation or the respiratory rate, can be extracted. In the illustrated example, a remote (RPPG) sensor integrated in a camera is illustrated. Such an RPPG sensor 41 makes use of an image sensor, as, e.g., comprised in a camera, in order to obtain a PPG waveform. It may also be possible that the camera sensor 32 is also used for obtaining the PPG waveform, i.e. that camera sensor 32 and PPG sensor 41 are integrated.

The different illustrated sensors may communicate with the system 10b through any kind of wired or wireless channel and continuously or sequentially provide their sensor signals. The sensors may be integrated in separate devices or multiple sensors may be integrated in a single device. If, e.g., the system 10b is implemented in the form of a handheld device such as a smartphone, this handheld device may include a Bluetooth or other wireless or wired communication interface that allows standard sensors to connect to and to provide their sensor signals. These sensor signals then at least partly form the sleep quality data based on which the sleep quality indicator and the machine operation settings are determined.

In another embodiment 10c of the system 10 according to the present invention, the system includes one or more of the sensors, i.e. one or more of the sensors are integrated with the system 10c. For instance, the illustrated safety support system 10c may include an (integrated) acceleration sensor 28', camera sensor 32', acoustic sensor 38', blood oxygenation sensor 40' and photoplethysmography sensor 41'. The illustrated embodiment 10c thus corresponds to a self-contained device including both the data processing as well as the sensor equipment in one device. Such device may particularly correspond to a handheld device, e.g. a smartphone or a wristband or the like. It may then be possible that a person makes use of a safety support system as described herein in form of a smartphone app. It may also be possible that a dedicated, i.e. separate, device is used.

Examples for devices or smartphone apps, respectively that provide information on the sleep quality mostly based on the evaluation of an acceleration sensor include Beddit (http://www.beddit.com/), Jawbone (https://jawbone.com/up), Fitbit (http://www.fitbit.com) and Sleep Cycle (http://www.sleepcycle.com/). These devices or apps may be used to provide a sensor signal to a system according to the present invention.

Figure 5:
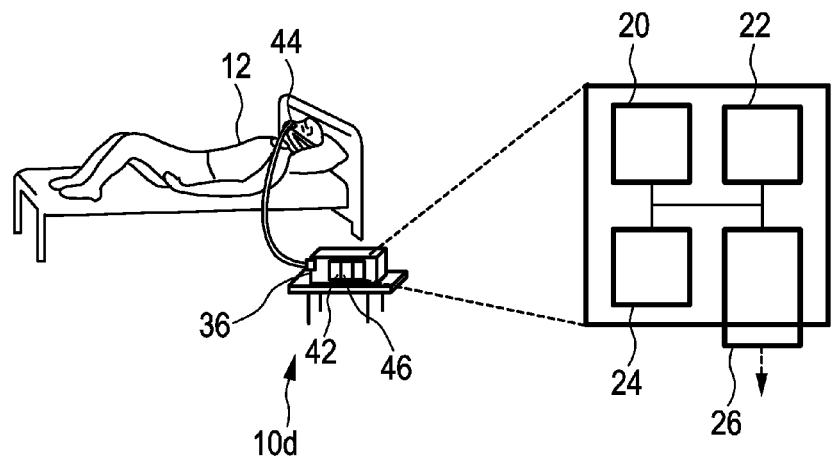
FIG. 5 illustrates a further embodiment of the system according to the present invention being integrated with a pressure support system.

FIG. 5 schematically illustrates yet another preferred embodiment 10d of the system 10 according to the present invention. According thereto, the system comprises a data interface 20, a sleep quality assessment unit 22, a safety unit 24 and a machine interface 26 as described above. In addition, the system 10d comprises a pressure support system 36 including a pressure generator 42, a patient interface 44 and a flow sensor 46. Therein, the pressure generator 42 may particularly include a pump. By means of this pump, a pressurized flow of breathable gas is generated. This pressurized flow is provided to the person 12 suffering from OSA through a patient interface 44. Such a patient interface 44 may particularly be represented by an air mask and be connected to the pressure generator by means of a hose or the like. The flow sensor 46 provides information on the breathing of the person 12. As indicated above, such information on the breathing may particularly include sensor signals indicative of how often a person breathes, how much support he/she requires, what kind of gas is provided, how often he/she suffers from apnea or hypopnea events, etc.

The illustrated system 10*d* thus corresponds to a PAP machine incorporating the additional safety support functionality according to the present invention.

Figure 6:
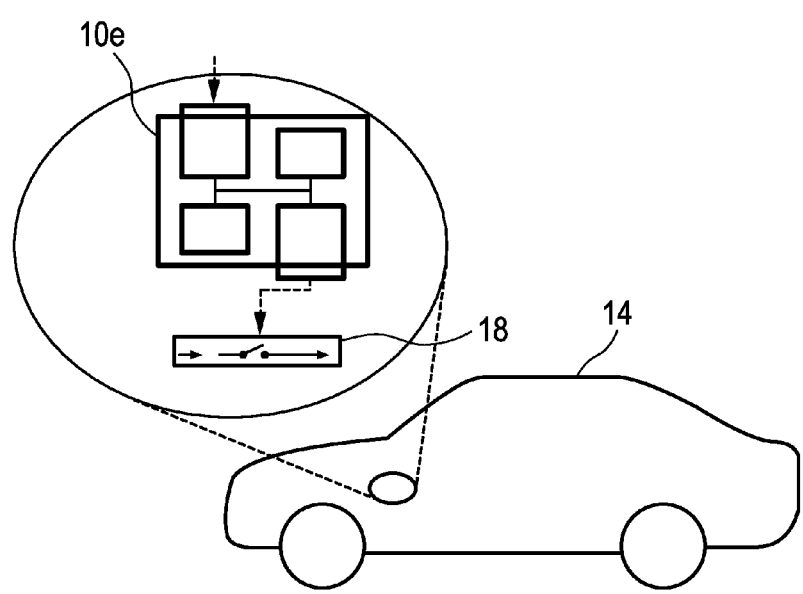
FIG. 6 schematically illustrates yet another embodiment of the system according to the present invention being integrated in a car.

FIG. 6 illustrates yet another embodiment 10*e* of the system 10 according to the present invention. Thereby, the system 10*e* is integrated in a machine 14 (a car in the illustrated example). Such a system 10*e* may, e.g., correspond to a subsequently integrated device incorporating the functionality according to the present invention. It may also be possible that a system according to the present invention is integrated a priori by the manufacturer of the machine 14. The system 10*e* thereby is connected to an interlock device 18 which allows restricting the operation of the machine 14, i.e. limiting the use, as indicated by the machine operation settings. The system 10*e* may also be integrated with the interlock device 18, i.e. include the interlock device 18.

The embodiment 10*e* may receive the required sleep quality data through the data interface from a handheld device communicating sensor data acquired during the night before. Alternatively, the system 10*e* may also receive data through an Internet connection as provided, e.g., by an Internet-capable PAP machine providing an AHI estimate or flow sensor data indicative of the breathing of a person.

The machine 14, may, e.g., require a specific code before it can be used, i.e. the interlock device may 18 function based on a code. The interlock device 18 could be part of the machine's 14 management system, or an additional device placed 'in-line' with the starter motor. Either the machine 14 or the 'in-line' device may have a network connection (e.g. Bluetooth) over which this code can be passed from a mobile device (e.g. smartphone, or key fob) to the machine 14 or 'in line' device.

Alternatively a safety support system 10 as disclosed herein may be integrated with a pressure support system. This safety support system 10 could issue a numeric code that the person has to enter into a key pad within the machine (code could be different each day, but possible to decrypt by the machine's systems). Furthermore, both the machine and the safety support system could be Internet-enabled and communicate directly. It may, e.g., be possible that the starter circuit of the machine 14 requires a wireless connection with a smartphone or other device and for the smartphone to give a secure code to start the machine 14. Depending on the determined machine operation settings the smartphone gives this or not. In another embodiment, a therapeutic device may directly determine whether it is safe for the person 12 to drive or not. If so, the therapeutic device may issue a software code to the smartphone via a network link. The smartphone then transmits this software code to the machine 14, with the machine 14 requiring it before it can be operated.

Figure 7:
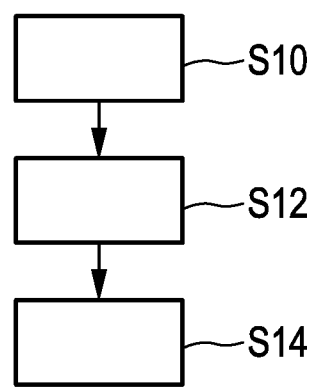
FIG. 7 schematically illustrates a safety support method according to an aspect of the present invention.

In FIG. 7, a method according to the present invention is schematically illustrated. This method includes the steps of receiving sleep quality data (step S10), determining based thereupon a sleep quality indicator (step S12) and determining machine operation settings based on the sleep quality indicator (step S14), said machine operation settings being indicative of an allowed operation of a machine by the person. Such a method may, e.g., be carried out on a personal computer, a microcontroller, an Internet server, a processor included in a pressure support system, a processor included in a machine, in particular a car, etc. The different method steps may particularly be interpreted as steps of a computer program.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A system configured to determine machine operation settings, the system comprising:
    a data interface for receiving sleep quality data carrying information on the sleep quality of a person;
    a sleep quality assessment unit for determining a sleep quality indicator indicative of the sleep quality of the person based on the received sleep quality data, wherein the sleep quality indicator is determined based on a number of apnea or hypopnea events; and
    a safety unit for determining machine operation settings prior to an intended operation of a machine by the person based on the sleep quality indicator, the machine operation settings being indicative of an allowed operation of the machine by the person,
    wherein the machine operation settings refer to restrictions or constraints on the operation of the machine and include values describing an accessible functional range defining which functions of the machine can be accessed by the person and to which extent each of the functions can be accessed, and
    wherein the machine operation settings include one or more of a maximum operation duration of the machine, a number of passengers permitted to be taken along with the person in the machine, a maximum load of the machine, an operation duration of the machine without rest, a driving velocity of the machine, a maximum operation speed of one or more moving parts of the machine, a minimum required resting time of the person while operating the machine, or a number and/or duration of required pauses for and/or surveillance of the person.

2. Safety support system as claimed in claim 1, further comprising a machine interface for communicating with the machine and for controlling the operation of the machine based on the determined machine operation settings.

3. Safety support system as claimed in claim 1, wherein the sleep quality data include data determined during a time period prior to an intended operation of the machine by the person.

4. Safety support system as claimed in claim 1, wherein the sleep quality data include a polysomnogram of the person that includes one or more signals representative of an electroencephalogram, an electrooculogram, an electromyogram, an electrocardiogram, an oral and/or nasal airflow, snoring loudness, a level of eye movement and a level of body movement.

5. The system as claimed in claim 1, wherein
the sleep quality data include data carrying direct or indirect information on apnea and hypopnea events during a sleep period of the person; and
the sleep quality assessment unit is configured to determine an estimate for an apnea-hypopnea-index of the person.

6. Safety support system as claimed in claim 1, wherein the sleep quality assessment unit is configured to determine the sleep quality indicator based on a neural network analysis.

7. Safety support system as claimed in claim 1, wherein the safety unit is configured to compare the determined sleep quality indicator with a threshold value.

8. Safety support system as claimed in claim 1, wherein
the data interface is configured to further receive medical history data of the person in addition to the sleep quality data, said medical history data being indicative of progress of a medical condition of the person; and
the sleep quality assessment unit is configured to determine the sleep quality indicator based on the received sleep quality data and the medical history data.

9. Safety support system as claimed in claim 1, further comprising at least one of the following sensors connected to the data interface for capturing at least one sensor signal, which at least one sensor signal at least partly forms the sleep quality data:
an acceleration sensor for capturing a sensor signal indicative of a movement of the person;
a camera sensor for capturing a sensor signal indicative of a movement of the eyes of the person;
a flow sensor for capturing a sensor signal indicative of the breathing of the person;
an acoustic sensor for capturing a sensor signal indicative of breathing sounds of the person;
a blood oxygenation sensor for capturing a sensor signal indicative of the blood oxygen saturation of the person; and
a photoplethysmography sensor for capturing a sensor signal indicative of a vital sign of the person.

10. Safety support system as claimed in claim 1, further comprising:
a pressure support system including:
a pressure generator for generating a pressurized flow of breathable gas;
a patient interface for delivering the pressurized flow of breathable gas to the person; and
a flow sensor for capturing a sensor signal indicative of the breathing of the person;
wherein the flow sensor is connected to the data interface and the sensor signal at least partly forms the sleep quality data.

11. Safety support system as claimed in claim 1, further comprising an interlock device for restricting the operation of a machine to the allowed operation based on the determined machine operation settings.

12. Machine comprising:
a safety system interface for communicating with a safety support system as claimed in claim 2 and for receiving machine operation settings being indicative of an allowed operation of the machine by a person, wherein said machine operation settings include a value which describes an accessible functional range defining which function of the machine can be accessed by the person and to which extent said function can be accessed; and
an interlock device for restricting the operation of the machine to the allowed operation based on said value included in the machine operation settings.

13. A method for determining machine operation settings, the method comprising:
receiving sleep quality data carrying information on the sleep quality of a person;
determining a sleep quality indicator indicative of the sleep quality of the person based on the received sleep quality data, wherein the sleep quality indicator is determined based on a number of apnea or hypopnea events; and
determining machine operation settings prior to an intended operation of a machine by the person based on the sleep quality indicator, the machine operation settings being indicative of an allowed operation of the machine by the person,
wherein the machine operation settings refer to restrictions or constraints on the operation of the machine and include values describing an accessible functional range defining which functions of the machine can be accessed by the person and to which extent each of the functions can be accessed, and
wherein the machine operation settings include one or more of a maximum operation duration of the machine, a number of passengers permitted to be taken along with the person in the machine, a maximum load of the machine, an operation duration of the machine without rest, a driving velocity of the machine, a maximum operation speed of one or more moving parts of the machine, a minimum required resting time of the person while operating the machine, or a number and/or duration of required pauses for and/or surveillance of the person.

14. A computer program comprising program code means for causing a computer to carry out the steps of the method as claimed in claim 13 when the computer program is carried out on the computer.

15. The system as claimed in claim 1, wherein the sleep quality indicator is determined based on the number of apnea events, the number of hypopnea events, and an amount of time the person was asleep.

16. The system as claimed in claim 1, further comprising:
a second data interface configured to facilitate reception of a secure code from a mobile device of the person such that the intended operation of the machine begins.

17. The method as claimed in claim 13, wherein the sleep quality indicator is determined based on the number of apnea events, the number of hypopnea events, and an amount of time the person was asleep.

* * * * *